US00PP16891P2

(12) United States Plant Patent
Utecht

(10) Patent No.: US PP16,891 P2
(45) Date of Patent: Jul. 25, 2006

(54) ***PELARGONIUM* PLANT NAMED 'FISORANGTAN'**

(50) Latin Name: *Pelargonium×hortorum*
Varietal Denomination: Fisorangtan

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 15 days.

(21) Appl. No.: 11/167,681

(22) Filed: Jun. 27, 2005

(51) Int. Cl.
*A01H 5/00* (2006.01)

(52) U.S. Cl. ..... Plt./327

(58) Field of Classification Search ..... Plt./327
See application file for complete search history.

*Primary Examiner*—Kent Bell
(74) *Attorney, Agent, or Firm*—Jondle & Associates, P.C.

(57) ABSTRACT

A new cultivar of *Pelargonium* particularly characterized by the combined features of large, salmon-orange, semi-double flowers, large inflorescences, dark green and slightly zoned foliage, a round and bushy plant habit with compact to medium growth, and an early to mid-season flowering response is disclosed.

1 Drawing Sheet

Figure 1:
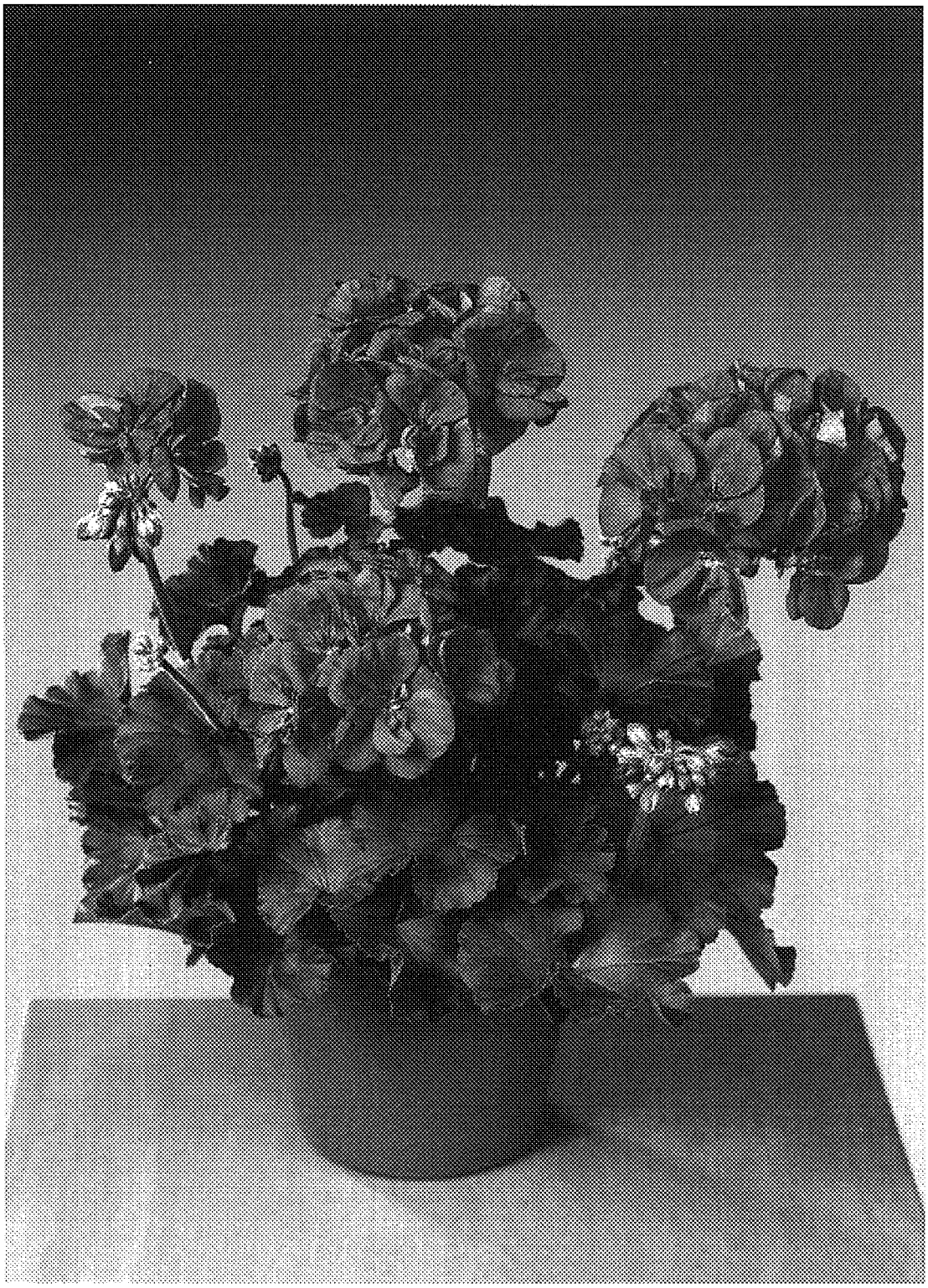

Genus and species: *Pelargonium×hortorum.*
Variety denomination: 'Fisorangtan'.

BACKGROUND OF THE NEW PLANT

The present invention comprises a new and distinct cultivar of *Pelargonium,* botanically known as *Pelargonium× hortorum,* a hybrid of *Pelargonium zonale* L'Héritier and hereinafter referred to by the cultivar name 'Fisorangtan'. The new cultivar is a product of a planned breeding program which had the objective of creating new varieties having orange, semi-double flowers, dark green, zoned foliage, and a well-branched growth habit with moderately vigorous growth. 'Fisorangtan' was discovered as a seedling resulting from a cross between the female parent, 'Fisrocky Orange' (U.S. Plant Pat. No. 12,365), which has orange, semi-double flowers, and dark green foliage with a narrow ring of zonation and the male parent, 'Dueimap' (U.S. Plant Pat. No. 13,241), which has bright orange, semi-double flowers, medium green foliage with weak zonation, and a compact to medium growth habit.

The new cultivar was created in 2000 in Hillscheid, Germany, and has been asexually reproduced repeatedly by vegetative cuttings in Galdar, Gran Canaria, Spain, and Hillscheid, Germany, over a four-year period. 'Fisorangtan' has not been observed under all possible environmental conditions, thus, the phenotype may vary significantly with variations in the environment such as temperature, light intensity, and day length. It has been found to retain its distinctive characteristics through successive asexual propagations. 'Fisorangtan' reproduces true to type in successive generations of asexual reproduction.

Plant Breeder's Rights for this cultivar were applied for in Germany on Jun. 2, 2004. No sales or offers for sale of this cultivar were made before early July 2004.

SUMMARY OF THE INVENTION

The following are the most outstanding and distinguishing characteristics of this new cultivar when grown under normal commercial practices in Hillscheid, Germany.

1. Large salmon-orange, semi-double flowers with good stability of flower color;
2. Large inflorescences on relatively short peduncles and no shattering of petals;
3. Dark green foliage with weak zonation;
4. Rounded and very well branched with a compact to medium plant habit;
5. A mid-season flowering response; and
6. Good stability of flower color and good rain resistance.

DESCRIPTION OF PHOTOGRAPH

This new *Geranium* plant is illustrated by the accompanying photograph which shows blooms, buds, and foliage of the plant; the colors shown are as true as can be reasonably obtained by conventional photographic procedures. The photograph is of a twelve-week-old plant grown from rooted cuttings, grown in 14-cm pots, left un-pinched, and grown under greenhouse conditions which approximate those generally used in commercial practice.

FIG. 1 shows overall plant habit with blooms, buds, and foliage.

DESCRIPTION OF THE NEW CULTIVAR

The following detailed descriptions set forth the distinctive characteristics of 'Fisorangtan'. The data which define these characteristics were collected from asexual reproductions carried out in Hillscheid, Germany. The plant history was taken on twelve-week-old, un-pinched plants grown in 14-cm pots in a greenhouse during mid-May. The color readings were determined under natural light in mid-May from flowers grown in a greenhouse. Color references are to The R.H.S. Colour Chart of The Royal Horticultural Society of London (R.H.S.) (2001).

DETAILED BOTANICAL DESCRIPTION

Classification:

*Botanical.—Pelargonium×hortorum,* a hybrid of *Pelargonium zonale* L'Héritier.

*Common name.*—*Geranium.*

*Parentage.*—Female parent: 'Fisrocky Orange' (U.S. Plant Pat. No. 12,365). Male parent: 'Dueimap' (U.S. Plant Pat. No. 13,241).

Plant:

*Branching habit.*—7 branches per plant.

*Height.*—12.8 cm for a 9 week-old plant (measured from base of stem to the tips of the branches, excluding the inflorescences).

*Width.*—23.8 cm for a 9 week-old plant.

*Time to produce a finished flowering plant.*—For spring flower response in Hillscheid, Germany, in 2004, 50% of the plants had open flowers after 8.5 weeks.

*Outdoor plant performance.*—Plants continuously flower; a flower count in mid-May of 2004 in Hillscheid, Germany indicated about 2.5 inflorescences per plant.

Leaves:

*Arrangement.*—Alternate.

*Immature leaf.*—Color: Upper surface: RHS 137A to 137B. Lower surface: RHS 137C.

*Mature leaf.*—Color: Upper surface: RHS 137A (dark green). Lower surface: RHS 137C. Length: 5.3 cm. Width: 8.0 cm.

*Zonation color.*—RHS 147A (deep green) to RHS 166A (brown) with weak distinctness.

*Zonation diameter.*—Inner ring is 4.3 cm while the band or belt is 1.5–2.0 cm wide.

*Apex.*—Rounded.

*Base description.*—Cordate.

*Shape.*—Kidney-shaped and distinctly wavy with an open gap between the lowest lobes.

*Margin.*—Bi-crenate.

*Texture.*—Upper surface is velvety and dull.

Petioles:

*Length.*—6.0–8.0 cm.

*Diameter.*—0.3–0.35 cm.

*Color.*—RHS 143B (light-green).

*Texture.*—Weak pubescence.

Stems:

*Length.*—7.0–8.0 cm.

*Internode length.*—1.0–1.5 cm.

*Color.*—RHS 143A (green).

*Texture.*—Appears smooth with slight pubescence.

Flower buds:

*Length.*—1.7 cm.

*Width.*—1.0 cm.

*Shape.*—Elliptical.

*Color of sepals* (*just before petals unfold*).—RHS 143A (light-green).

*Color of petals* (*just before petals unfold*).—RHS 40A.

Inflorescence:

*Type.*—An umbel composed of 25–30 flowers.

*Umbel diameter.*—10.0 cm.

*Umbel depth* (*height*).—5.8 cm.

*Umbel shape.*—Initially umbrella-shaped, later becoming semi-spherical.

*Lastingness of umbel on the plant.*—16–18 days.

*Peduncle.*—Length: 14.6 cm. Diameter: 5.0–7.0 mm. Texture: Covered with weak pubescence. Color: Between RHS 143C (light-green) and RHS 143B (light-green).

*Pedicel.*—Length: 2.3 cm. Diameter: 1.5 mm. Texture: Weak pubescence. Color: RHS 143B (light-green) but RHS 176A (brown) near upper end.

Corolla:

*Diameter.*—5.2 cm.

*Form.*—Semi-double.

*Shape.*—Oval to nearly round outline, wide cup-shaped with a few inner petals.

*Number of petals.*—7–9.

*Petaloids.*—Number: 0.2. Shape: Narrow. Color: RHS 41A.

*Lastingness of individuals flowers on the plant.*—8 days at 18° C.

*Fragrance.*—None.

Petals:

*Upper petals.*—Length: 3.0–3.2 cm. Width: 2.0–2.7 cm. Color: Upper surface: Mainly RHS 41A but RHS 41B to RHS 41C near base, mature flowers may fade to RHS 43C. Lower surface: RHS 41B (orange) but slightly variable. Markings: Faint macule, RHS 52A (carmine-pink).

*Lower petals.*—Length: 2.8–2.9 cm. Width: 2.6–2.7 cm. Color: Upper surface: RHS 40B. Lower surface: RHS 41B (orange) but slightly variable. Markings: Absent.

*Shape.*—Obovate.

*Apex.*—Rounded.

*Base.*—Acute.

*Margin.*—Entire.

*Texture.*—Smooth and slightly glossy.

Sepals:

*Number.*—5.

*Length.*—1.0–1.2 cm.

*Width.*—0.4 cm for the largest upper sepal and 0.2–0.3 cm for the other sepals.

*Shape.*—Linear to lanceolate.

*Apex.*—Acute.

*Base.*—Truncate.

*Margin.*—Entire.

*Texture.*—Very weak pubescence.

*Color.*—For both the upper and lower surfaces, mainly RHS 143A (light-green) with RHS 179A (brown) near the base.

Reproductive organs:

*Androecium.*—Number of anthers: 7. Filament color: RHS 155D (white). Filament length: 7.0 mm. Pollen color: RHS 28A (yellow-orange). Pollen amount: Abundant.

*Gynoecium.*—Pistil number: 1. Pistil length: 7.0 mm. Stigma color: RHS 43C (salmon-pink). Stigma shape: 5–6 lobed. Style color: RHS 43C (salmon-pink). Style length: 3.0–4.0 mm. Style shape: Filiform with the lobes of the stigma at a right angle.

Fruit/seed set: No seed set observed.

Disease and insect resistance: Average/typical susceptibility and tolerance and no special observations made.

COMPARISON WITH KNOWN CULTIVARS

Of the many commercial cultivars known to the present inventor, the most similar in comparison to 'Fisorangtan' are the related varieties 'Fisrocky Orange' (U.S. Plant Pat. No. 12,365) and 'Dueimap' (U.S. Plant Pat. No. 13,241) and the commercial cultivar 'Gensoran' (unpatented).

Cultivar 'Fisorangtan' differs from the female parent 'Fisrocky Orange' (U.S. Plant Pat. No. 12,365) in that 'Fisorangtan' has a somewhat deeper and more brilliant flower color and exhibits very little fading. Additionally, the upper surface of the leaves of 'Fisorangtan' exhibits a slightly weaker and narrower zonation than that of 'Fisrocky Orange'.

Cultivar 'Fisorangtan' differs from the male parent 'Dueimap' (U.S. Plant Pat. No. 13,241) in that the flowers of 'Fisorangtan' are less orange in color and the foliage is darker green than that of 'Dueimap'.

Cultivar 'Fisorangtan' differs from the commercial comparison variety 'Gensoran' (unpatented) in that the flower color of 'Gensoran' is a more brilliant orange and the inflorescences are composed of more, but smaller flowers Additionally, the peduncles of 'Gensoran' are partly reddish (on the side of the peduncle), while the peduncles of 'Fisorangtan' are mainly green with a weak infusion of brown near the upper end.

I claim:

1. A new and distinct cultivar of *Pelargonium* plant as shown and described herein.

* * * * *